United States Patent
Krause

(10) Patent No.: US 11,173,066 B2
(45) Date of Patent: Nov. 16, 2021

(54) DEVICE FOR DEFINING A FLAP GEOMETRY

(71) Applicant: Alcon Inc., Fribourg (CH)

(72) Inventor: Johannes Krause, Erlangen (DE)

(73) Assignee: Alcon Inc., Fribourg (CH)

( * ) Notice: Subject to any disclaimer, the term of this patent is extended or adjusted under 35 U.S.C. 154(b) by 865 days.

(21) Appl. No.: 15/088,648

(22) Filed: Apr. 1, 2016

(65) Prior Publication Data

US 2016/0324691 A1     Nov. 10, 2016

(30) Foreign Application Priority Data

May 8, 2015   (DE) .......................... 102015006041.4

(51) Int. Cl.
    *A61F 9/008*     (2006.01)

(52) U.S. Cl.
    CPC ...... *A61F 9/00802* (2013.01); *A61F 9/00836* (2013.01); *A61F 2009/00872* (2013.01); *A61F 2009/00878* (2013.01); *A61F 2009/00882* (2013.01)

(58) Field of Classification Search
    CPC combination set(s) only.
    See application file for complete search history.

(56) References Cited

U.S. PATENT DOCUMENTS

| | | | |
|---|---|---|---|
| 2007/0235543 A1* | 10/2007 | Zadoyan | A61F 9/00825 235/462.01 |
| 2008/0051769 A1 | 2/2008 | Mrochen et al. | |
| 2011/0224657 A1 | 9/2011 | Stevens et al. | |
| 2011/0295244 A1 | 12/2011 | Mrochen et al. | |
| 2012/0083775 A1 | 4/2012 | Donitzky et al. | |
| 2014/0135747 A1 | 5/2014 | Donitzky et al. | |
| 2014/0316389 A1* | 10/2014 | Schuele | A61F 9/00804 606/5 |

FOREIGN PATENT DOCUMENTS

| | | |
|---|---|---|
| EP | 1834615 A1 | 9/2007 |
| JP | 2012521228 A | 9/2012 |
| JP | 2012-521228 A | 9/2013 |
| WO | 2012/041352 A1 | 4/2012 |

* cited by examiner

*Primary Examiner* — Scott Luan

(57) ABSTRACT

A device for defining a flap geometry of a flap for laser treatment of a human eye comprises a control unit programmed to evaluate ablation profile data of an ablation profile for a laser ablation treatment of a human cornea and to define the flap geometry based on this evaluation.

11 Claims, 4 Drawing Sheets

DEVICE FOR DEFINING A FLAP GEOMETRY

CROSS REFERENCE TO RELATED APPLICATIONS

This application claims priority to German Patent Application Serial Number 102015006041.4, filed 8 May 2015, titled "DEVICE FOR DEFINING A FLAP GEOMETRY," which is hereby incorporated by reference in its entirety.

TECHNICAL FIELD

The present disclosure relates in general to a device for defining a flap geometry. It relates in particular to a device for defining a flap geometry of a flap for laser treatment of the human eye (LASIK flap).

BACKGROUND

A so-called LASIK (laser in-situ keratomileusis) technique is often used for the correction of defective vision of the human eye (for example, myopia, hyperopia, or astigmatism). In this procedure, first a small corneal cover disk (referred to in general as a flap) is cut from the adjacent corneal tissue, where the flap remains adhering the surrounding corneal tissue in the hinge region. This makes it possible to simply fold the flap over to expose the underlying tissue regions of the cornea and simply folding the flap back over after ablation of the exposed tissue regions. Removal of material by focused UV laser radiation in ablation results in an altered shape of the corneal surface after the flap has been folded back over, and therefore this alters the refractive properties of the cornea and consequently of the overall ophthalmic system. By suitable definition of the ablation profile, a vision deficiency can at least be definitely diminished and at best even eliminated almost completely.

To be able to correct an individual patient's faulty vision, it is necessary to determine an individual ablation profile for each of the patient's eyes. Furthermore, the geometry of the flap to be cut (size, position, orientation) must be defined for each of the patient's eyes, but this involves a great deal of effort on the part of the physician operating the cutting laser.

SUMMARY OF EXEMPLARY EMBODIMENTS

One object of the present invention is to simplify the definition of the flap geometry.

One aspect of the present invention is a device for defining a flap geometry of a flap for laser treatment of a human eye, comprising a control unit, which is programmed to evaluate ablation profile data of an ablation profile for a laser ablation treatment of a human cornea and define the flap geometry based on this evaluation.

The control unit may be a program-controlled control unit, which may comprise a processor, a volatile memory and/or a nonvolatile memory, for example. Programming of the control unit may be performed by writing a corresponding program to a memory of the control unit, for example. A program in a memory in the control unit can be executed by a processor of the control unit. During execution of the program, the aforementioned steps can be carried out. The ablation profile data of the ablation profile may be present in the form of digital data, for example, in the form of a data file. The ablation profile data may describe the desired ablation profile for the ablation treatment of the eye of the patient to be treated. The ablation profile data may be contained in a data file, for example, which indicates, pixel-by-pixel, a depth value for a two-dimensional matrix of pixels. The depth value may be a value (in μm or nm, for example), to which the human cornea is to be ablated by an ablation laser during the laser ablation treatment. The ablation profile data may be in the form of vectors. The ablation profile data can establish a spatial relationship between the ablation profile and the eye to be treated in. For example, a reference point, which corresponds to the midpoint of the pupil of the eye to be treated, may be defined in the ablation profile data. Furthermore, a reference axis, which corresponds to a horizontal axis and/or a vertical axis of the eye to be treated, can also be defined in the ablation profile data. Evaluation of the ablation profile data may include a software-supported evaluation. For this evaluation, for example, known methods may be used for the image processing and/or the image evaluation. The flap geometry can best be defined on the basis of the evaluation, so that certain result values and/or analytical data of the analytical process can be used to define the flap geometry. The flap geometry may be defined in such a way that corresponding data representing the flap geometry is written to a memory of the control unit. Flap geometry data, which is written to a memory of the control unit, may be determined on the basis of the defined flap geometry.

The control unit may be programmed such that evaluating the ablation profile data comprises determining a diameter of the ablation profile and such that defining the flap geometry comprises defining a diameter of the flap based on the diameter of the ablation profile.

The diameter of the ablation profile can be determined with the help of known methods of image processing, for example. The diameter of the ablation profile may be a diameter, which is determined in top view. "In top view," as used below, means that an x-y plane of the ablation profile and/or the flap geometry is considered. The x-y plane may essentially correspond to the surface of the human cornea, which is leveled by a contact element during the process of cutting a flap. The x-y plane may correspond to a plane that is perpendicular to a z axis. The z axis may essentially correspond to the incident direction of a cutting laser and/or an ablation laser. The z axis may correspond to a radial direction of the eyeball, which runs through the midpoint of the pupil. The diameter may be, for example, the maximum diameter of the ablation profile. The diameter may further be, for example, the diameter along a predetermined axis, for example, along a horizontal or vertical axis of the ablation profile. The horizontal axis and/or the vertical axis of the ablation profile may correspond to a horizontal and/or vertical axis of the eye to be treated. The definition of the diameter of the flap may be such that the flap is essentially circular in a view from above and the diameter of the circle is defined as a function of the specific diameter of the ablation profile. The diameter of the circle of the flap may be larger by a predetermined value than the determined diameter of the ablation profile.

The control unit may be programmed such that defining the flap geometry is performed in consideration of a defined safety margin, such that in top view a shortest distance between an outer edge of the ablation profile and an outer edge of the flap at each location amounts to at least the safety margin.

The safety margin may be a length value (in μm, for example), which may be defined by the user of the device (for example, a physician). The safety margin may be stored together with the ablation profile data in a data file and read out of this data file.

The control unit may be programmed such that evaluating the ablation profile data comprises determining the position of the ablation profile with respect to the eye to be treated and such that defining the flap geometry comprises defining a position of the flap with respect to the eye to be treated.

The ablation profile data may include information about the position of the ablation profile with respect to the eye to be treated. For example, it may include information about the position of the ablation profile with respect to the midpoint of the pupil of the eye to be treated. If the ablation profile data is available in the form of a pixel-based data file, for example, then a predetermined pixel of the data file may correspond to the position of the midpoint of the pupil of the eye to be treated. The flap may be essentially circular or essentially oval, for example, in top view. The flap may have a hinge on one side. Defining the position of the flap with respect to the eye to be treated may include, for example, defining the position of the midpoint of the essentially circular flap with respect to the eye to be treated.

The control unit may be programmed such that evaluating the ablation profile data comprises determining an orientation of the ablation profile with respect to the eye to be treated and such that defining the flap geometry comprises defining an orientation of the flap with respect to the eye to be treated.

The ablation profile data may include information about the orientation of the ablation profile with respect to the eye to be treated. For example, it may also include information about the orientation of the ablation profile with respect to the horizontal or vertical axis of the eye to be treated. This may include, for example, angle information or an angle value. For determining the orientation of the ablation profile, the ablation profile data may include a reference axis, for example, which corresponds to the horizontal or vertical axis of the eye to be treated. Defining the orientation of the flap may include a definition of the orientation of rotation of the flap with respect to the horizontal or vertical axis of the eye to be treated. The flap may be essentially circular or essentially oval in a view from above. The flap may have a hinge on one side.

The control unit may be programmed such that defining the orientation of the flap comprises defining a position of a hinge of the flap with respect to the eye to be treated.

The position of the hinge may be defined, for example, such that a shortest distance from the hinge to an outer edge of the ablation profile is at its maximum in top view.

The control unit may be programmed such that evaluating the ablation profile data comprises determining a diameter of the ablation profile and determining an axis, along which the ablation profile has the greatest diameter, and wherein defining the flap geometry comprises defining an orientation of the hinge of the flap parallel to the axis.

The control unit may be programmed such that evaluating of the ablation profile data comprises determining an axis of mirror symmetry of the ablation profile, and wherein defining the flap geometry comprises defining an orientation of a hinge of the flap perpendicular to the axis of mirror symmetry.

The axis of mirror symmetry may be an axis with respect to which the ablation profile is essentially in mirror symmetry. The ablation profile may have one or two axes of mirror symmetry, for example. The axis of mirror symmetry may be determined so that it corresponds to an axis, which itself corresponds most closely to an axis of mirror symmetry of the ablation profile. In other words, the axis of mirror symmetry may be an axis with respect to which there is the greatest possible mirror symmetry of the ablation profile.

The orientation of the hinge of the flap perpendicular to the axis of mirror symmetry may be carried out in such a way that mirror symmetry of the flap corresponds essentially to mirror symmetry of the ablation profile. The orientation of the hinge of the flap may be defined in such a way that the axis of mirror symmetry of the flap corresponds to the axis of mirror symmetry of the ablation profile.

The control unit may be programmed such that evaluating the ablation profile data comprises determining a depth of the ablation profile and defining the flap geometry comprises defining a thickness of the flap based on the depth of the ablation profile.

The depth may be determined along the z axis (along the incident direction of the cutting laser and/or the ablation laser). The depth of the ablation profile may correspond to the thickness of the corneal tissue to be ablated by the ablation laser. The specific depth of the ablation profile may be, for example, the maximum depth of the ablation profile. In other words, it may be the depth at the deepest point of the ablation profile. The thickness of the flap may be the thickness along the z direction. The thickness of the flap may be defined in such a way that, for example, a greater specific depth of the ablation profile leads to a smaller defined thickness of the flap and vice versa.

The control unit may be programmed such that defining the flap geometry is performed in consideration of a corneal thickness and/or at least one curvature radius of the cornea of the eye to be treated.

The flap geometry may be defined, for example, such that a higher value of the corneal thickness leads to a higher value of the defined thickness of the flap and vice versa. Conversely the thickness of the flap may be defined so that the sum of the thickness of the flap, the maximum depth of the ablation profile and a predetermined safety distance corresponds to the thickness of the cornea.

The device may also comprise an input interface for reading in the ablation profile data.

The input interface may include, for example, a network interface and/or an interface for reading from a memory medium. The memory medium may be, for example, a magnetic memory medium, an optical memory medium or a semiconductor memory medium. The network interface may be connected to the Internet, for example, and/or to an internal network (intranet). A network interface of an ablation laser, for example, may be connected to the network. The ablation profile data in the form of a data file, for example, may be entered via the input interface. The input interface may comprise a network interface, which is connected to a network, and the ablation profile data can be retrieved from a database, which is located in a memory of a server or some other device connected to the network, for example, via the network interface.

The control unit may also be programmed to determine flap geometry data based on the defined flap geometry.

The flap geometry data may be present in the form of a data file and/or individual parameters, for example. The parameters may be written to a database, for example. The parameters of the flap geometry data may comprise at least one of the following parameters, for example: flap diameter, flap thickness, position of the midpoint of the flap with respect to the midpoint of the pupil of the eye to be treated and the orientation of the flap (for example, in the form of an angle) with respect to a reference axis of the eye to be treated. In addition or as an alternative to the parameters, the entire shape of the flap (for example, its contour and/or cut edges) may be saved as a data file. The flap geometry data may be stored, for example, in a pixel-based data file or a vector-based data file. The flap profile data can establish a spatial relationship between the flap and the eye to be treated. For example, a reference point, which corresponds to the midpoint of the pupil of the eye to be treated, may be defined in the flap geometry data. Furthermore, a reference axis, which corresponds to a horizontal axis and/or a vertical axis of the eye to be treated, may be defined in the flap geometry data. Furthermore, the flap geometry data can be written to a data file together with the ablation profile data of the eye to be treated.

The device may further comprise an output interface for outputting the flap geometry data.

The flap geometry data can be output via the output interface to a cutting laser, which then cuts a flap corresponding to the flap geometry data into the eye to be treated. The output interface may comprise a network interface and/or an interface for reading from a memory medium, for example. The memory medium may be, for example, a magnetic memory medium, an optical memory medium and/or a semiconductor memory medium. The network interface may be connected, for example, to an internal network (intranet) and/or to the Internet.

Another aspect of the present invention is a cutting laser for cutting a flap for laser treatment of a human eye, comprising the device described herein.

The control unit of the device may be, for example, a control unit of the cutting laser which is programmed accordingly. The flap geometry may be forwarded directly to the cutting laser in the form of flap geometry data, for example.

BRIEF DESCRIPTION OF THE DRAWINGS

Additional features, advantages and components of the present invention can be found in the following description of the accompanying drawings, in which:

FIG. 3b shows an example of a flap geometry that has been defined on the basis of the ablation profile shown in FIG. 3a;

FIG. 4b shows an example of a flap geometry, which has been defined on the basis of the ablation profile shown in FIG. 4a.

DETAILED DESCRIPTION OF EXEMPLARY EMBODIMENTS

Figure 1:
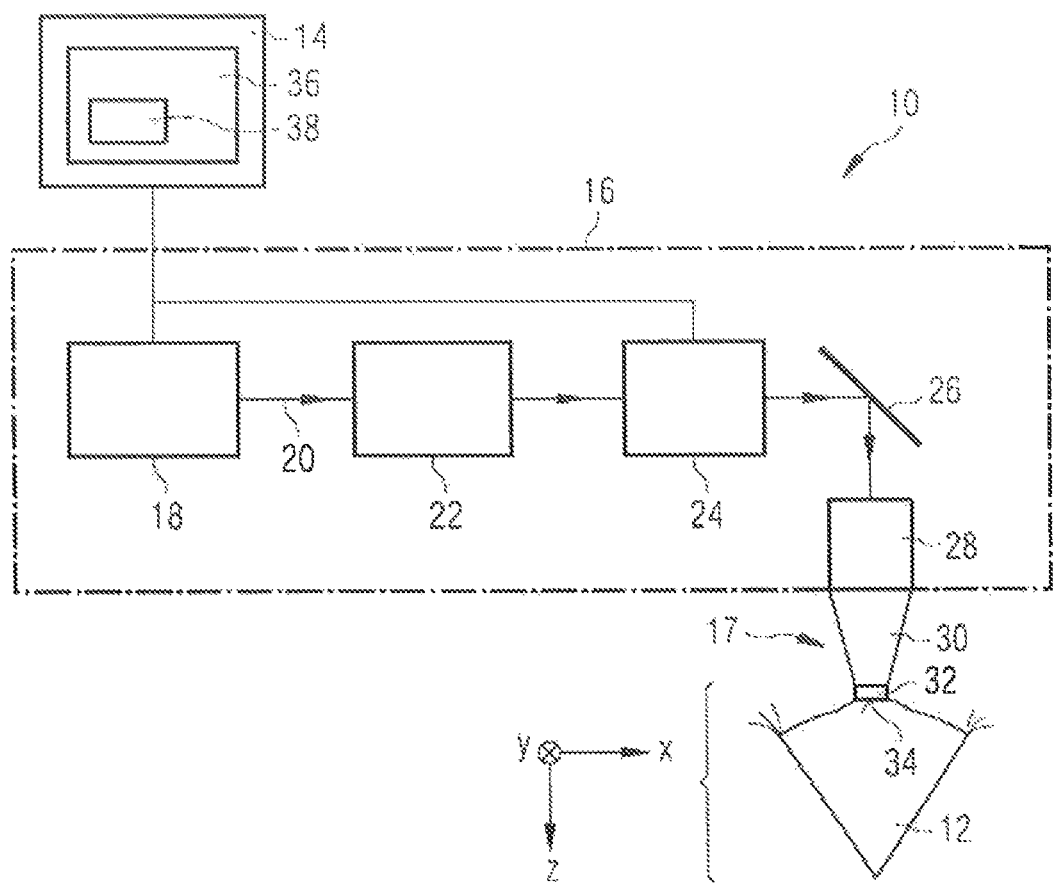
FIG. 1 shows a schematic block diagram of an exemplary embodiment of a cutting laser for laser treatment of a human eye.

FIG. 1 shows a block diagram of an exemplary embodiment of a device labeled as 10 in general for laser treatment of a human eye 12. The device 10 is a cutting laser for laser treatment of a human eye. The device 10 comprises a control unit 14, a laser configuration 16 and a patient adapter 17.

The laser configuration 16 comprises a laser source 18, which generates a laser beam 20 having pulse durations in the femtosecond range, for example. The laser beam 20 has a wavelength suitable for generating a laser-induced optical breakdown in the corneal tissue of the eye 12. The laser beam 20 may have a wavelength in the range of 300 nm (nanometers) to 1900 nm, for example, a wavelength in the range of 300 nm to 650 nm, 650 nm to 1050 nm, 1050 nm to 1250 nm or 1100 nm to 1900 nm. The laser beam 20 may also have a focus diameter of 5 µm or less.

A beam widening lens system 22, a scanner unit 24, a mirror 26 and a focusing lens system 28 are positioned behind the laser source 18 in the direction of propagation of the laser beam 20 (indicated by the arrows in FIG. 1). The beam widening lens system 22 serves to increase the diameter of the laser beam 20 generated by the laser source 18. In the exemplary embodiment shown here, the beam widening lens system 22 is a Galileo telescope having a concave lens (lens with a negative refractive power) and a convex lens (lens with a positive refractive power) positioned behind the concave lens in the direction of propagation of the laser beam 20. These may be a plano-concave lens or a piano-convex lens, which has planar sides facing one another. In another exemplary embodiment, the beam widening lens system may comprise a Kepler telescope having two convex lenses, for example, as an alternative to the Galileo telescope.

The scanner unit 24 is designed to control the position of the focus of the laser beam 20 (beam focus) in the transverse direction and in the longitudinal direction. The transverse direction describes the direction transverse to the direction of propagation of the laser beam 20 (labeled as the x-y plane) and the longitudinal direction describes the direction of propagation of the laser beam 20 (labeled as the z direction). The scanner unit 24 may comprise, for example, a pair of galvanometrically operated deflecting mirrors for transverse deflection of the laser beam 20; these mirrors can be tilted about mutually perpendicular axes. Alternatively or additionally, the scanner unit 24 may have an electro-optical crystal or some other components suitable for transverse deflection of the laser beam 20. The scanner unit 24 may also comprise a longitudinally adjustable or refractive lens of a variable power or a deformable mirror to influence the divergence of the laser beam 20, and consequently, the longitudinal orientation of the beam focus. In the exemplary embodiment shown here, the components for control of the transverse orientation and longitudinal orientation of the beam focus are represented as an integral component. In another exemplary embodiment, the components may be arranged separately along the direction of propagation of the laser beam 20. Thus, for example, an adjustable mirror may be arranged in the direction of propagation upstream from the beam widening lens 22 for control of the longitudinal orientation of the beam focus.

The mirror 26 is a stationary deflecting mirror, which is designed to deflect the laser beam 20 in the direction of the focusing lens system 28. Additionally or alternatively, other optical mirrors and/or optical elements may also be positioned in the beam path for deflection and diffraction of the laser beam 20.

The focusing lens system 28 is designed to focus the laser beam 20 on the region of the cornea of the eye 12 to be treated. The focusing lens system 28 may be an F-theta lens system, for example. The focusing lens system 28 is detachably connected to the patient adapter 17. The patient adapter 17 comprises a conical carrier sleeve 30, which is connected to the focusing lens system 28 by a coupling formation (not shown), and a contact element 32, which is mounted on the narrower bottom side of the carrier sleeve 30 facing the eye 12. The contact element 32 may be attached to the carrier sleeve 30 either permanently (for example, by adhesive bonding) or detachably (for example, by screw connection). The contact element 32 has a bottom side which faces the eye 12 and is labeled as a contact surface 34. In the exemplary embodiment shown here, the contact surface 34 is designed as a planar surface. In the laser treatment of the eye 12, the contact element 32 is pressed against the eye 12 or a vacuum is applied to the eye 12 on the contact surface 34, such that at least the region of the cornea of the eye 12 that is to be treated is leveled and lies in the x-y plane.

The control unit 14 comprises a memory 36, in which at least one control program 38 having program instructions is stored. The laser source 18 and the scanner unit 24 are controlled by the control unit 14 in accordance with the program instructions. The control program 38 contains program instructions, which, when executed by the control unit 14, cause the beam focus to move in space and time in such a way that a cutting patter is created in the cornea of the eye 12 to be treated. The cutting pattern may comprise a LASIK flap. Data defining the shape of the cutting pattern may be stored in the form of flap geometry data in the memory 36 of the control unit 14 and retrieved therefrom. The flap geometry data may have previously been loaded into the memory 36 of the control unit 14 with the help of a network interface of the control unit, for example. However, the flap geometry data may also be entered manually via a corresponding input interface of the control unit (using a keyboard, for example).

Figure 2:
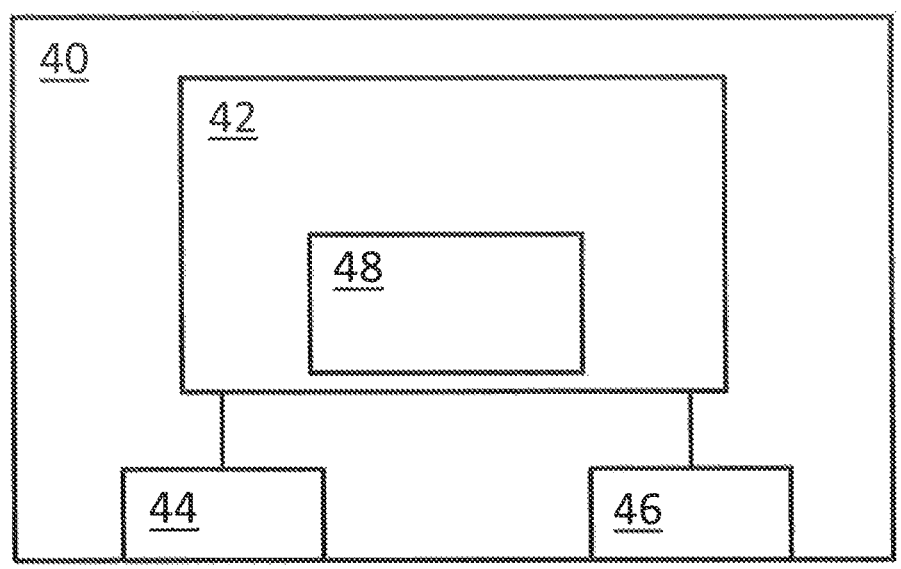
FIG. 2 shows an exemplary embodiment of a device for defining the flap geometry of a flap for laser treatment of the human eye.

FIG. 2 shows a schematic block diagram of one exemplary embodiment of a device 40 for defining the flap geometry of a flap for laser treatment of the human eye. The device 40 comprises a control unit 42, an input interface 44 and an output interface 46. Ablation profile data for evaluation by the control unit 42 can be input via the input interface 44. Flap geometry data generated by the control unit 42 can be output via the output interface 46. The input interface 44 and the output interface 46 may each comprise, for example, a network interface connected to a conventional network for data exchange between terminals. A server, a network memory, a cutting laser and/or an ablation laser, for example, may be connected to the network to exchange data with one another. The network may be the Internet, for example, or an intranet within the treatment practice. Additionally or alternatively, however, the input interface 44 may also have a direct input option, such as a keyboard interface, for example. Additionally or alternatively, the output interface 46 may have a direct output option, such as a screen interface, for example. Furthermore, both the input interface 44 and the output interface 46 may comprise an interface for reading from and/or writing to a memory medium. The memory medium may be a magnetic memory medium, an optical memory medium and/or a semiconductor memory medium.

The control unit 42 comprises a memory 48. The memory 48 comprises a volatile memory and/or a nonvolatile memory. The memory 48 is used for temporary storage of calculations of the control unit 42 and can also store ablation profile data and flap geometry data. Furthermore, a control program, comprising commands for evaluating ablation profile data of an ablation profile for a laser ablation treatment of a human cornea and for defining a flap geometry on the basis of the evaluation, is also stored in the memory 48.

The control unit 42 may be, for example, the control unit 14 of the cutting laser 10 shown in FIG. 1 and the memory 48 may be the memory 36 of the control unit 14. The device 40 for defining a flap geometry may thus be provided at the cutting laser 10, which has the advantage that the flap geometry, defined by the control unit 42, is directly available to the user of the cutting laser 10 (a physician) for cutting the respective flap. However, the control unit 42 may also be provided at an ablation laser, wherein the memory 48 may be, for example, a memory of the ablation laser, in which ablation profile data for the eyes to be treated is stored. This has the advantage that the respective ablation profile data is directly available to the control unit 42. However, the device 40 may also be provided as an independent device, which reads in ablation profile data via the input interface 44 and outputs flap geometry data via the output interface 46.

The control unit 42 also comprises a processor (not shown) for executing the program instructions of the control program stored in the memory 48.

Ablation profile data for a laser ablation treatment of a human cornea of an eye to be treated is entered via the input interface 44. For example, if the control unit 42 is provided at the ablation laser, the ablation profile data may alternatively also be read directly out of the memory 48 and the input interface 44 is optional in this case. The ablation profile data may be present, for example, in the form of a data file or some other data record. For example, the ablation profile data, like a gray scale image data file may have a two-dimensional matrix of pixels, with a depth value (gray scale value) assigned to each pixel. The depth value here corresponds to the desired depth of ablation at the respective location of the pixel, which is identified by x-y coordinates. Regions of the x-y plane, in which no ablation is to take place, can also be defined within the ablation profile data. These regions are not considered below as part of the ablation profile. When speaking of a size and/or diameter of the ablation profile below, for example, only the region of the ablation profile in which ablation is to take place via the ablation laser is being considered.

To establish a spatial reference for the ablation profile data with respect to the eye to be treated, at least one fixed point and at least one reference axis may be defined in the ablation profile data. The fixed point may be, for example, the midpoint of the pupil of the eye to be treated. The reference axis may be, for example, a horizontal or vertical axis of the eye to be treated. For example, it is possible to stipulate that a certain pixel value of the x-y plane corresponds to the midpoint of the pupil of the eye to be treated. Furthermore, it is possible to provide that a horizontal pixel axis, for example, corresponds to the horizontal axis of the eye to be treated.

The ablation profile data may also be in the form of vector-based data or in any other data format that makes it possible to represent an ablation profile that is to be implemented with respect to an eye to be treated.

The control unit 42 analyzes the ablation profile data and defines a flap geometry for a flap to be cut by the cutting laser 10 on the basis of this evaluation. Details of the evaluation and the definition are described further below with reference to FIGS. 3a to 4b. On the basis of the flap geometry, flap geometry data that is output via the output interface 46 is generated by the control unit 42. If the device 40 is part of the cutting laser, then the flap geometry data may for example only be written to the memory 48, from which it can be retrieved by the cutting laser 10. The output interface 46 is optional in this case. The flap geometry data is suitable for uniquely defining the flap geometry to be cut by the cutting laser 10. In particular the flap geometry data comprises an outline of the flap in top view (in the x-y plane) and the thickness of the flap to be cut. The flap geometry data may be available in the form of a data file or parameters, for example, wherein the parameters are suitable for determining the flap geometry uniquely. The corresponding parameters may thus comprise, for example, a value for the diameter of the flap in top view and an angle value for the orientation of the hinge of the flap.

Figure 3A:
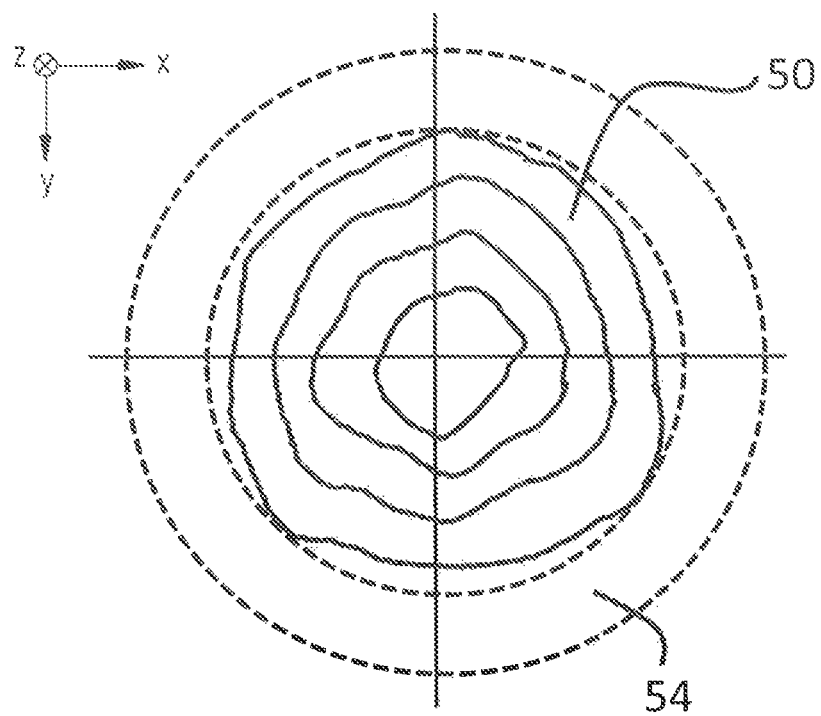
FIG. 3a shows an example of an ablation profile and a respective safety margin.
Figure 3B:
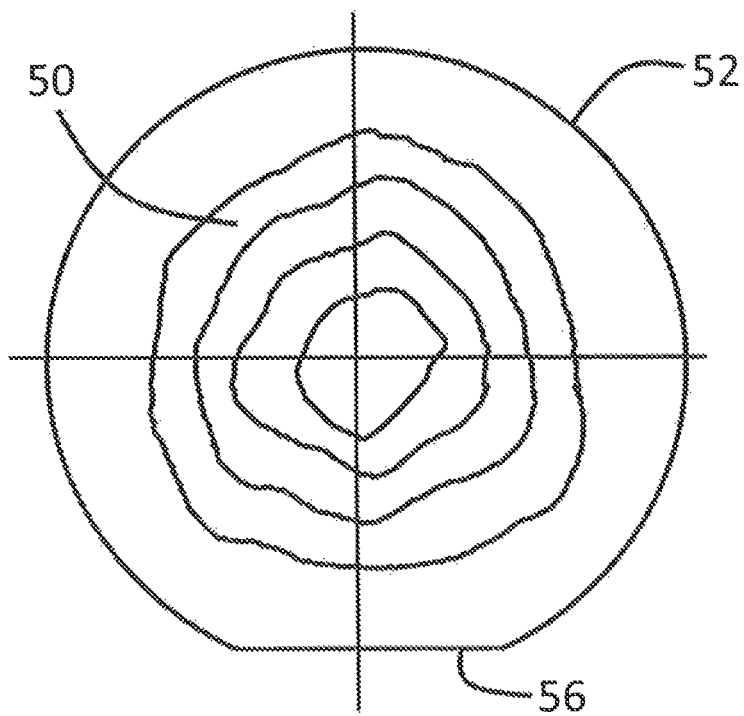

FIG. 3a shows schematically a first example of an ablation profile 50, and FIG. 3b shows the outline of a flap 52, which is defined by the control unit 42 of the device 40 on the basis of the ablation profile 50. FIGS. 3a and 3b (as well as FIGS. 4a and 4b, which are described further below) show the ablation profile 50 and the flap 52 in top view, wherein the plane of the drawing corresponds to the x-y plane (see also FIG. 1). The depth of the ablation profile 50 in the z direction is indicated by depth lines (isobaths). Each of the depth lines runs along a plane extending parallel to the x-y plane at a constant distance. Thus each of the depth lines of the ablation profile 50 runs along a constant depth of the ablation profile 50. The outermost one of the depth lines indicates an exterior outline of the ablation profile 50. In other words, no ablation takes place outside of the outermost line of the ablation profile 50, and when speaking of the ablation profile 50 below, the region inside the outermost depth line of the ablation profile 50 is intended.

A horizontal line in the x direction and a vertical line in the y direction indicate a coordination system within the x-y plane. The position and orientation of the ablation profile 50 with respect to the eye to be treated can both be identified on the basis of the coordination system. The horizontal line in the x direction, for example, corresponds to the horizontal axis of the eye to be treated, and the point of intersection of the vertical line and the horizontal line identify the midpoint of the pupil of the eye to be treated. A patient's vision can be compensated accurately and reliably by indicating the ablation profile 50 with respect to this coordinate system. In the case of astigmatism in the patient's eye in particular, it is necessary to provide ablation profile data indicating the position and the orientation (rotational orientation) of the ablation profile 50.

FIG. 3a also shows a safety zone 54, in which the flap 52 can be defined as follows: First, the midpoint and the diameter of a circle is determined; this is the circle with the smallest diameter into which the ablation profile 50 fits, in top view, without the outer edge of the ablation profile 50 protruding beyond the circle (internal dotted line circle in FIG. 3a). Furthermore, a value defined previously (for example, by the physician operating the cutting laser 10) for a safety margin is also taken into account. This value is added to the radius of the first circle, resulting in a larger second circle with the same midpoint as that of the first circle (see outer circle, shown with a dotted line in FIG. 3a). As shown in FIG. 3b, the flap 52 is then defined, so that the cutting edge essentially follows the second circle in top view. This ensures that the cutting edge of the flap 52 is at a distance from the outer edge of the ablation profile 50 by a corresponding safety margin 54 at all points. In other words, this ensures that the shortest distance between the outer edge of the ablation profile 50 and the outer edge of the flap 52 in top view amounts to at least the safety margin of the safety zone 54 at all points.

The flap geometry of the flap 52 also comprises a hinge 56, which is represented as a straight line in FIG. 3b. The hinge 56 of the flap 52 does not represent a cutting edge of the flap 52, but instead is a joint of corneal tissue along which the cutting laser 10 does not make a cut. Providing a hinge 56 makes it possible to fold the flap 52 over and to accurately fold the flap 52 back after the ablation treatment so that the flap tissue is essentially in the same position on the x-y plane before and after the ablation treatment. The position of the hinge 56 may be defined manually (by providing the proper parameters) by the user, so that it is always either in a lower position (see FIG. 3b) or in an upper position of the flap 52, for example. The hinge 56 may be set parallel to the horizontal axis along the x direction, for example. Furthermore, the position of the hinge 56 may be automatically defined by the control unit 42 on the basis of the ablation profile data for the ablation profile 50 (see also the example of FIGS. 4a and 4b). For example, the position of the hinge 56 may be defined in such a way that the shortest distance from the hinge 56 to the outer edge of the ablation profile 50 exceeds a predetermined value, so that a safety margin is maintained between the hinge 56 and the ablation profile 50.

Furthermore, within the context of the definition of the flap geometry, the thickness of the flap 52 in the z direction may be defined on the basis of the evaluation of the ablation profile data. For example, the ablation profile data may be analyzed in such a way that the maximum depth of the ablation profile is determined. The thickness of the flap 52 is then defined so that the sum of the maximum depth of the ablation profile and the thickness of the flap 52 does not exceed a predetermined value. It is possible herein to ensure that the laser treatment is performed only in a certain region of the cornea and that the underlying tissue of the eye is not damaged. For the definition of the thickness, for example, a previously determined value for the thickness of the cornea of the eye to be treated may be taken into account. The thickness of the flap 52 may be defined, for example, so that the sum of the thickness of the flap 52, the maximum depth of the ablation profile 50 and a predetermined safety distance corresponds to the thickness of the cornea of the eye to be treated.

Furthermore, at least one curvature radius of the cornea of the eye to be treated can be taken into account in determining the flap geometry.

Figure 4A:
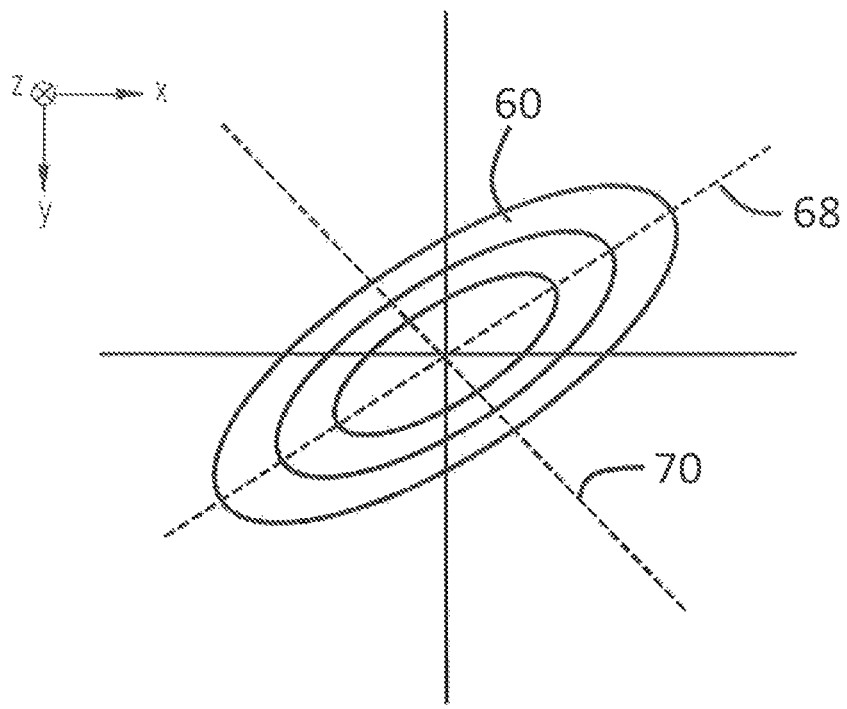
FIG. 4a shows an example of an ablation profile and respective axes.
Figure 4B:
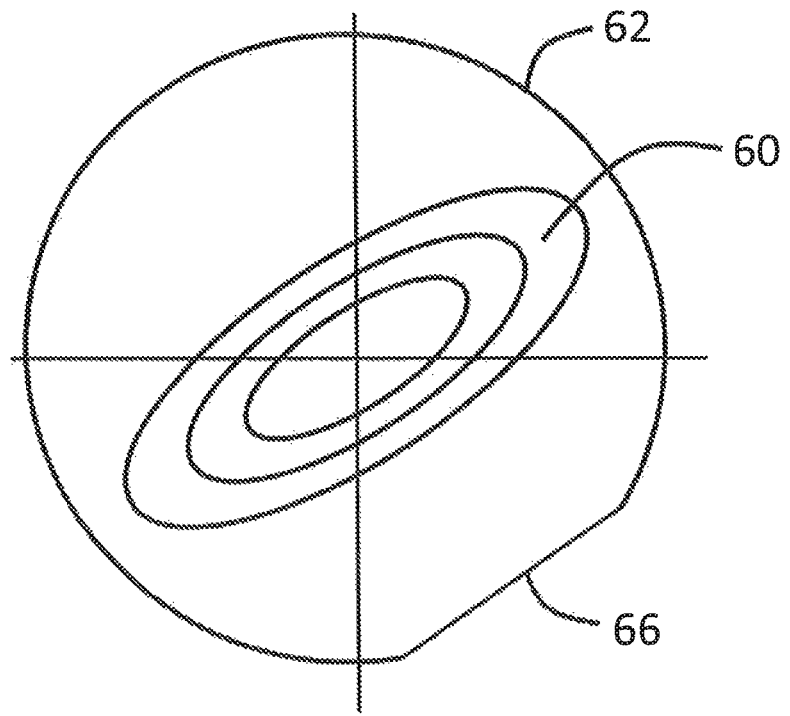

FIG. 4a shows a second example of an ablation profile 60 and FIG. 4b shows a flap geometry of a flap 62 defined on the basis of an evaluation of the ablation profile 60. For FIGS. 4a and 4b, the same principles apply as those described previously in conjunction with FIGS. 3a and 3b. In particular a corresponding safety margin may be taken into account in the definition of the flap 62.

FIG. 4a shows an example of an ablation profile 60 of a patient with a severe astigmatism (curvature of the cornea). The ablation profile 60 here is far away from a point symmetry, but it has two mutually perpendicular mirror symmetry axes 68 and 70. The position of the mirror symmetry axes 68 and 70 with respect to the eye to be treated varies from one patient to the next and is part of the individual vision defect to be corrected.

The orientation of the flap 62 in FIG. 4b is selected so that the hinge 66 of the flap 62 is parallel to the mirror symmetry axis 68 and perpendicular to the mirror symmetry axis 70. The mirror symmetry of the flap 62 thus corresponds to the mirror symmetry of the ablation profile 60 with respect to the mirror symmetry axis 70. This has the advantage that, when cutting the flap 62 with the cutting laser 10, no additional asymmetries are created with regard to the mirror symmetry in relation to the mirror symmetry axis 70.

In evaluating the ablation profile 60, the mirror symmetry axis 68 and/or the mirror symmetry axis 70 of the ablation profile is/are determined. For example, the axis 60 may be determined, so that there is a search for the axis along which the ablation profile 60 will have the greatest diameter (axis 68 in the example of FIG. 4a). The position of the hinge 66 of the flap 62 is then defined so that the hinge 66 runs parallel to the axis 68.

Furthermore, the axis 68 and/or the axis 70 can be determined by considering the symmetry properties of the ablation profile 60. For example, it is possible to search for the axis with respect to which the ablation profile 60 will have the greatest possible mirror symmetry. It should be pointed out here that the case of perfect mirror symmetry, as represented in FIG. 4a, occurs very rarely in reality and there may be minor deviations with regard to the mirror symmetry. For example, the ablation profile may either have no preferential mirror symmetry axis at all, just one preferred mirror symmetry axis or two preferred mirror symmetry axes, in which case the first mirror symmetry axis runs essentially perpendicular to the second mirror symmetry axis (see FIG. 4a). In evaluation of the ablation profile data of the ablation profile 60, for example, the mirror symmetry axis 70 can be determined and the flap geometry can be defined as shown in FIG. 4a, so that the hinge 66 of the flap 62 is perpendicular to the mirror symmetry axis 70. The mirror symmetry of the flap 62 thus corresponds essentially to the previously determined mirror symmetry of the ablation profile 60. Although essentially circular flap geometries are illustrated in FIGS. 3b and 4b, the shape of the flap in top view is not limited to a circle but can also exhibit an oval shape or an essentially rectangular shape.

With the help of the device described herein, the flap geometry can be defined automatically and individually on the basis of ablation profile data analyzed automatically in advance. Valuable time can be saved here in the preparation for the laser ablation treatment and the flap geometry can be defined reliably and without error.

The invention claimed is:

1. A device for defining a flap geometry of a flap for laser treatment of a human eye, comprising:
   a laser source of a cutting laser, the laser source configured to generate a laser beam having pulse durations in the femtosecond range, the laser beam suitable for generating an optical breakdown in a human cornea;
   a scanner unit of the cutting laser, the scanner unit configured to control a focus of the laser beam in a transverse direction and in a longitudinal direction; and
   a control unit programmed to:
      evaluate ablation profile data of an ablation profile for a laser ablation treatment of the cornea, the ablation profile describing ablation of the cornea by an ablation laser, the evaluating comprising determining a diameter of the ablation profile;
      define the flap geometry based on the evaluation according to:
         a diameter of the flap based on the diameter of the ablation profile that describes ablation of the cornea;
         a defined safety margin stored with the ablation profile, such that in top view a shortest distance between an outer edge of the ablation profile and an outer edge of the flap at each location amounts to at least the safety margin; and
         a position of a hinge of the flap such that a shortest distance from the hinge to an outer edge of the ablation profile amounts to at least the safety margin; and
      instruct the scanner unit of the cutting laser to control the focus of the laser beam to cut the flap with the flap geometry in a cornea of the human eye.

2. The device of claim 1, wherein:
   evaluating the ablation profile data comprises determining a position of the ablation profile with respect to the eye to be treated; and
   defining the flap geometry comprises defining a position of the flap with respect to the eye to be treated.

3. The device of claim 1, wherein:
   evaluating the ablation profile data comprises determining an orientation of the ablation profile with respect to the eye to be treated; and
   defining the flap geometry comprises defining an orientation of the flap with respect to the eye to be treated.

4. The device of claim 3, wherein defining the orientation of the flap comprises defining a position of a hinge of the flap with respect to the eye to be treated.

5. The device of claim 1, wherein:
   evaluating the ablation profile data comprises determining an axis along which the ablation profile has the greatest diameter; and
   defining the flap geometry comprises defining an orientation of the hinge of the flap parallel to the axes.

6. The device of claim 1, wherein:
   evaluating the ablation profile data comprises determining an axis of mirror symmetry of the ablation profile; and
   defining the flap geometry comprises defining an orientation of a hinge of the flap perpendicular to the axis of mirror symmetry.

7. The device of claim 1, wherein:
   defining the flap geometry is performed in consideration of a corneal thickness or at least one curvature radius of the cornea of the eye to be treated.

8. The device of claim 1, further comprising:
   an input interface for reading in the ablation profile data.

9. The device of claim 1, wherein the control unit is further programmed to determine flap geometry data based on the defined flap geometry.

10. The device of claim 9, further comprising:
    an output interface for outputting the flap geometry data.

11. The device of claim 1 wherein the outer edge of the flap exceeds the outer edge of the ablation profile by the safety margin.

* * * * *